United States Patent
Smith

(10) Patent No.: US 8,282,663 B2
(45) Date of Patent: Oct. 9, 2012

(54) BLADELESS OBTURATOR FOR USE IN A SURGICAL TROCAR ASSEMBLY

(75) Inventor: Robert C. Smith, Middletown, CT (US)

(73) Assignee: Tyco Healthcare Group LP, Mansfield, MA (US)

( * ) Notice: Subject to any disclaimer, the term of this patent is extended or adjusted under 35 U.S.C. 154(b) by 616 days.

(21) Appl. No.: 12/194,629

(22) Filed: Aug. 20, 2008

(65) Prior Publication Data
US 2009/0093833 A1    Apr. 9, 2009

Related U.S. Application Data

(60) Provisional application No. 60/998,016, filed on Oct. 5, 2007.

(51) Int. Cl.
*A61B 17/34* (2006.01)

(52) U.S. Cl. ........................ 606/190; 606/185

(58) Field of Classification Search .............. 606/185, 606/190, 184, 172, 108, 44, 158; 604/44, 604/158, 164.01, 166, 170, 190, 506.19, 604/523; 600/114; 407/53, 54; 408/68, 408/230

See application file for complete search history.

(56) References Cited

U.S. PATENT DOCUMENTS

| | | |
|---|---|---|
| 4,535,773 A | 8/1985 | Yoon |
| 4,601,710 A | 7/1986 | Moll |
| 4,654,030 A | 3/1987 | Moll et al. |
| 5,066,288 A | 11/1991 | Deniega et al. |
| 5,104,382 A | 4/1992 | Brinkerhoff et al. |
| 5,215,526 A | 6/1993 | Deniega et al. |
| 5,224,952 A | 7/1993 | Deniega et al. |
| 5,226,891 A | 7/1993 | Bushatz et al. |
| 5,232,440 A | 8/1993 | Wilk |
| 5,248,298 A | 9/1993 | Bedi et al. |
| 5,314,417 A | 5/1994 | Stephens et al. |
| 5,364,372 A | 11/1994 | Danks et al. |
| 5,366,445 A | 11/1994 | Haber et al. |
| 5,372,588 A | 12/1994 | Farley et al. |
| 5,387,197 A | 2/1995 | Smith et al. |
| 5,399,167 A * | 3/1995 | Deniega ............. 604/164.12 |
| 5,411,515 A | 5/1995 | Haber et al. |
| 5,471,705 A | 12/1995 | Dao |
| 5,478,317 A | 12/1995 | Yoon |

(Continued)

FOREIGN PATENT DOCUMENTS

EP      E 0 604 197       6/1994

(Continued)

OTHER PUBLICATIONS

European Search Report for EP 08253185.6-2310 date of completion is Feb. 8, 2010 (3 pages).

*Primary Examiner* — Ryan Severson
*Assistant Examiner* — Rachel S Papeika

(57) ABSTRACT

An obturator assembly comprising an obturator housing, an obturator member and an obturator sleeve is disclosed. The obturator member is mounted to the obturator housing, defines a longitudinal axis, and has proximal and distal ends. The obturator member includes an interchangeable obturator rod and a penetrating end. The penetrating end defines a substantially planar dissecting segment and a central rod segment extends from the planar dissecting element. The obturator sleeve is coaxially mounted about the obturator member and is adapted for reciprocal longitudinal movement between a retracted position and an extended position.

18 Claims, 10 Drawing Sheets

U.S. PATENT DOCUMENTS

| | | | |
|---|---|---|---|
| 5,487,745 A | 1/1996 | McKenzie | |
| 5,522,833 A | 6/1996 | Stephens et al. | |
| 5,533,977 A | 7/1996 | Metcalf et al. | |
| 5,538,509 A | 7/1996 | Dunlap et al. | |
| 5,545,150 A | 8/1996 | Danks et al. | |
| 5,554,137 A | 9/1996 | Young et al. | |
| 5,554,167 A | 9/1996 | Young et al. | |
| 5,569,160 A | 10/1996 | Sauer et al. | |
| 5,607,440 A | 3/1997 | Danks et al. | |
| 5,609,604 A | 3/1997 | Schwemberger et al. | |
| 5,624,459 A | 4/1997 | Kortenbach et al. | |
| 5,658,236 A | 8/1997 | Sauer et al. | |
| 5,669,885 A | 9/1997 | Smith | |
| 5,676,156 A | 10/1997 | Yoon | |
| 5,690,663 A | 11/1997 | Stephens | |
| 5,690,664 A | 11/1997 | Sauer et al. | |
| 5,697,913 A | 12/1997 | Sierocuk et al. | |
| 5,709,671 A | 1/1998 | Stephens et al. | |
| 5,772,660 A | 6/1998 | Young et al. | |
| 5,776,112 A | 7/1998 | Stephens et al. | |
| 5,797,943 A | 8/1998 | Danks et al. | |
| 5,824,002 A * | 10/1998 | Gentelia et al. | 604/164.11 |
| 5,827,315 A | 10/1998 | Yoon | |
| 5,843,115 A | 12/1998 | Morejon | |
| 5,860,996 A | 1/1999 | Urban et al. | |
| 5,868,773 A | 2/1999 | Danks et al. | |
| 5,879,332 A | 3/1999 | Schwemberger et al. | |
| 5,893,369 A | 4/1999 | LeMole | |
| 5,904,699 A | 5/1999 | Schwemberger et al. | |
| 5,913,848 A | 6/1999 | Luther et al. | |
| 5,916,232 A | 6/1999 | Hart | |
| 5,947,930 A | 9/1999 | Schwemberger et al. | |
| 5,980,493 A | 11/1999 | Smith et al. | |
| 5,984,941 A | 11/1999 | Wilson et al. | |
| 5,997,510 A | 12/1999 | Schwemberger | |
| 6,017,356 A | 1/2000 | Frederick et al. | |
| 6,022,367 A | 2/2000 | Sherts | |
| 6,030,402 A | 2/2000 | Thompson et al. | |
| 6,036,657 A | 3/2000 | Milliman et al. | |
| 6,063,099 A | 5/2000 | Danks et al. | |
| 6,228,058 B1 | 5/2001 | Dennis et al. | |
| 6,319,226 B1 | 11/2001 | Sherry | |
| 6,319,266 B1 * | 11/2001 | Stellon et al. | 606/185 |
| 6,497,687 B1 | 12/2002 | Blanco | |
| 6,497,716 B1 | 12/2002 | Green et al. | |
| 6,544,277 B1 | 4/2003 | O'Heeron et al. | |
| 6,613,063 B1 | 9/2003 | Hunsberger | |
| 6,656,198 B2 * | 12/2003 | Tsonton et al. | 606/167 |
| 6,685,630 B2 | 2/2004 | Sauer et al. | |
| 6,716,201 B2 | 4/2004 | Blanco | |
| 6,719,746 B2 | 4/2004 | Blanco | |
| 6,830,578 B2 | 12/2004 | O'Heeron et al. | |
| 6,835,201 B2 | 12/2004 | O'Heeron et al. | |
| 6,837,874 B1 * | 1/2005 | Popov | 604/164.06 |
| 6,960,164 B2 | 11/2005 | O'Heeron | |
| D518,177 S | 3/2006 | Blanco | |
| D531,726 S | 11/2006 | Blanco et al. | |
| 7,320,694 B2 * | 1/2008 | O'Heeron | 606/167 |
| 7,344,519 B2 * | 3/2008 | Wing et al. | 604/167.03 |
| 7,758,603 B2 * | 7/2010 | Taylor et al. | 606/185 |
| 2003/0100914 A1 | 5/2003 | O'Heeron et al. | |
| 2003/0109894 A1 | 6/2003 | Blanco | |
| 2004/0230155 A1 | 11/2004 | Blanco et al. | |
| 2004/0230217 A1 | 11/2004 | O'Heeron | |
| 2005/0033304 A1 | 2/2005 | O'Heeron | |
| 2005/0038466 A1 | 2/2005 | O'Heeron et al. | |
| 2005/0065543 A1 * | 3/2005 | Kahle et al. | 606/190 |
| 2005/0107816 A1 * | 5/2005 | Pingleton et al. | 606/185 |
| 2005/0119676 A1 | 6/2005 | Bumbalough et al. | |
| 2005/0203559 A1 * | 9/2005 | O'Heeron | 606/185 |
| 2005/0209623 A1 | 9/2005 | Patton | |
| 2005/0261717 A1 | 11/2005 | Sauer et al. | |
| 2006/0030870 A1 | 2/2006 | Staudner | |
| 2006/0149302 A1 | 7/2006 | Popov | |
| 2006/0173479 A1 | 8/2006 | Smith | |
| 2006/0200095 A1 | 9/2006 | Steube | |
| 2006/0200182 A1 | 9/2006 | Prosek | |
| 2007/0005087 A1 | 1/2007 | Smith et al. | |
| 2007/0010842 A1 | 1/2007 | Popov | |
| 2007/0016237 A1 | 1/2007 | Smith | |

FOREIGN PATENT DOCUMENTS

| | | |
|---|---|---|
| WO | WO 94-04082 | 3/1994 |

* cited by examiner

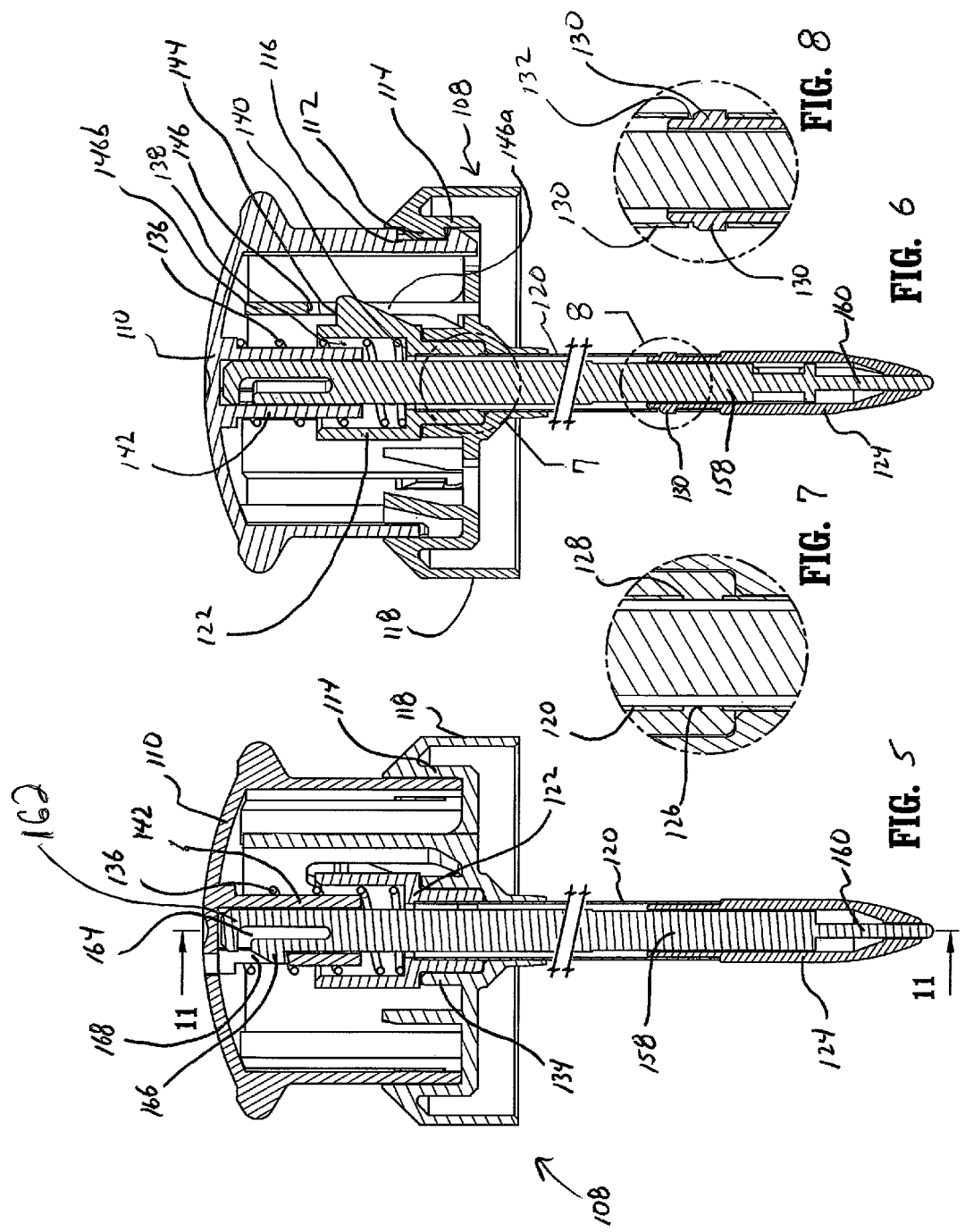

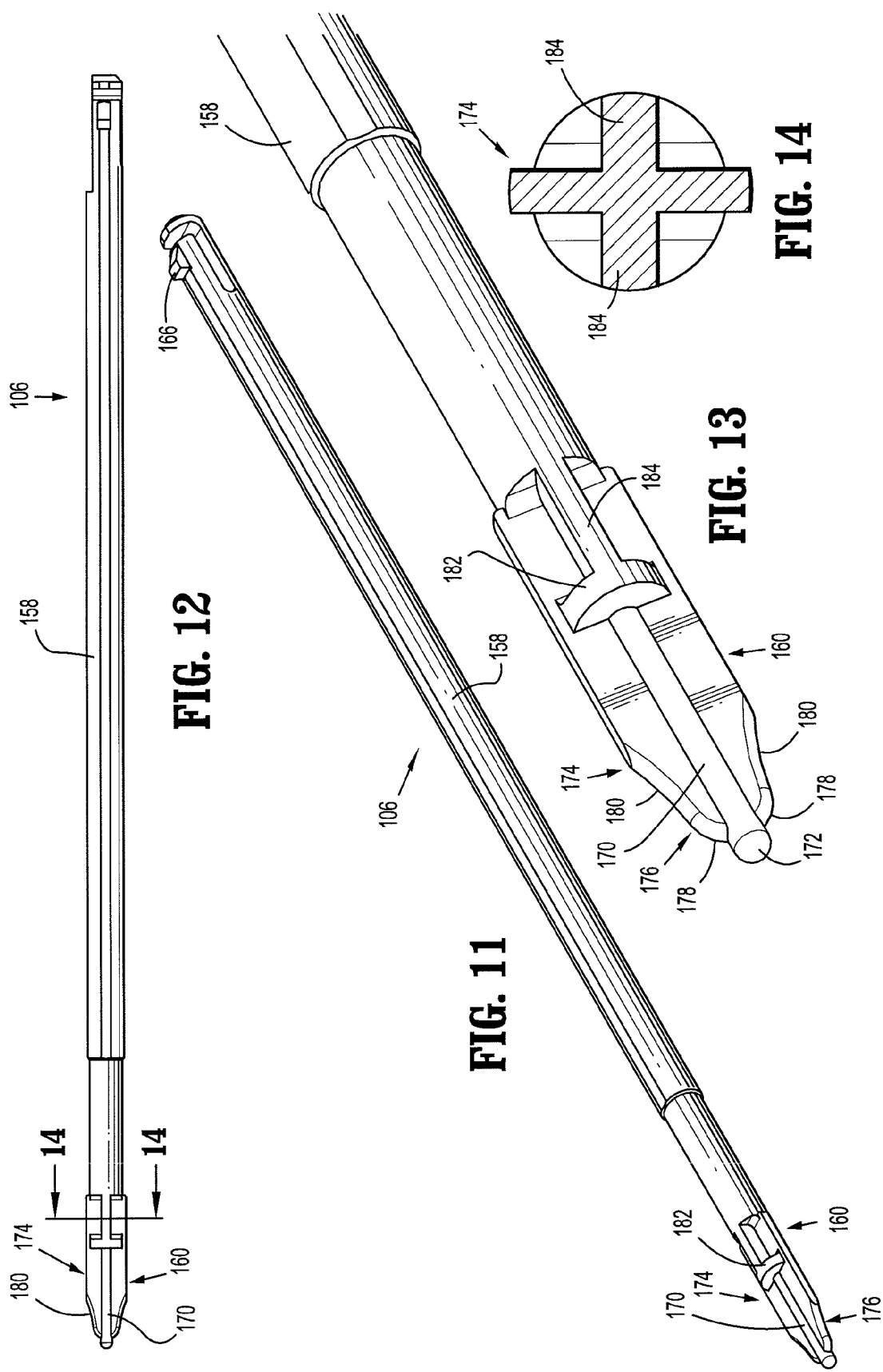

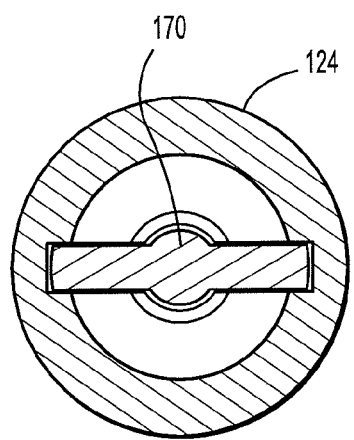 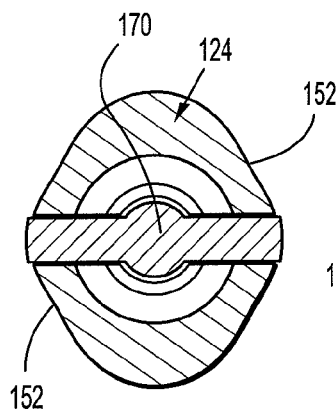 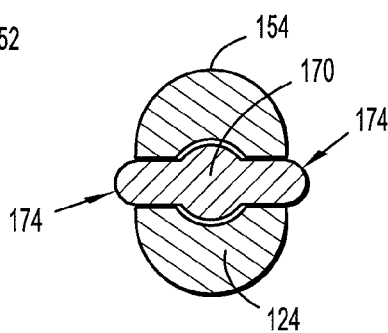
FIG. 15  FIG. 16  FIG. 17

BLADELESS OBTURATOR FOR USE IN A SURGICAL TROCAR ASSEMBLY

CROSS REFERENCE TO RELATED APPLICATION

The present application claims the benefit of and priority to U.S. Provisional Application Ser. No. 60/998,016 filed on Oct. 5, 2007, the entire contents of which are incorporated herein by reference.

BACKGROUND

1. Technical Field

The present disclosure relates to an obturator assembly for use in minimally invasive surgical procedures, such as endoscopic or laparoscopic type procedures.

2. Background of the Related Art

Minimally invasive procedures are continually increasing in number and variation. Forming a relatively small diameter temporary pathway to the surgical site is a key feature of most minimally invasive surgical procedures. The most common method of providing such a pathway is by inserting a trocar assembly through the skin. In many procedures, the trocar assembly is inserted into an insufflated body cavity of a patient. In such procedures, the trocar assemblies with seal mechanisms are utilized to provide the necessary pathway to the surgical site while minimizing leakage of insufflation gases.

Trocar assemblies typically include an obturator which is removably inserted through a cannula. The obturator may include a safety shield which protects against unintentional puncturing by the sharpened tip of the obturator. The safety shield includes a mechanism which controls the relative movement and locking of the safety shield. One example of a safety shield mechanism is disclosed in commonly assigned U.S. Pat. No. 6,319,266 to Stellon et al., the entire contents of which are hereby incorporated by reference.

SUMMARY

Accordingly, the present disclosure is directed to an obturator assembly for use in dissection of tissue. The obturator includes an obturator housing, an obturator member mounted to the obturator housing and an obturator sleeve coaxially mounted about the obturator member and adapted for reciprocal longitudinal movement between a retracted position and an extended position. The obturator member includes an obturator rod and a penetrating end. The penetrating end defines a substantially planar dissecting segment and a central rod segment extending from the planar dissecting element. The planar segment of the penetrating end of the obturator member defines atraumatic outer edges which may be arcuate in character. The central rod segment defines a distal entry surface which is also atraumatic, and may be arcuate as well. In one embodiment, the distal entry surface of the central rod segment and the atraumatic edges of the planar dissecting segment are at least partially exposed from the nose shield when in the extended position of the obturator sleeve. The obturator sleeve may include a generally tapered nose shield for at least partially accommodating the penetrating end.

BRIEF DESCRIPTION OF THE DRAWINGS

Preferred embodiments of the present disclosure are described hereinbelow with references to the drawings, wherein:

FIG. 5 is a side cross-sectional view of the obturator assembly taken along the lines 5-5 of FIG. 3;

FIG. 6 is a second side cross-sectional view of the obturator assembly;

FIG. 7 is an enlarged view of the indicated area of detail of FIG. 6;

FIG. 8 is an enlarged view of the indicated area of detail of FIG. 6;

FIG. 11 is a perspective view of the obturator member illustrating the obturator rod and the obturator penetrating head;

FIG. 12 is a side plan view of the obturator member;

FIG. 13 is an enlarged perspective view of the obturator penetrating head;

FIG. 14 is a cross-sectional view of the obturator rod taken along the line 14-14 of FIG. 12;

FIG. 15 is a cross-sectional view taken along the lines 15-15 of FIG. 9;

FIG. 16 is a cross-sectional view taken along the lines 16-16 of FIG. 9;

FIG. 17 is a cross-sectional view taken along the lines 17-17 of FIG. 9;

DETAIL DESCRIPTION OF PREFERRED EMBODIMENTS

Figure 1:
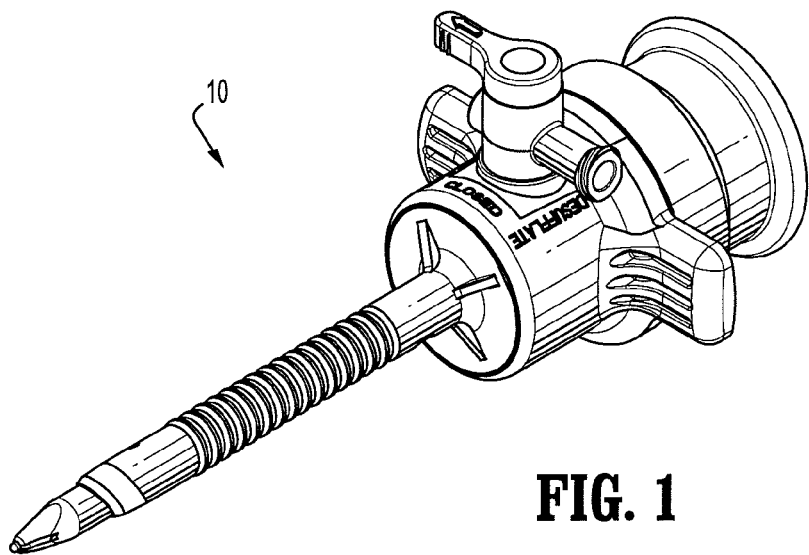
FIG. 1 is a perspective view of a trocar assembly in accordance with the present disclosure.
Figure 2:
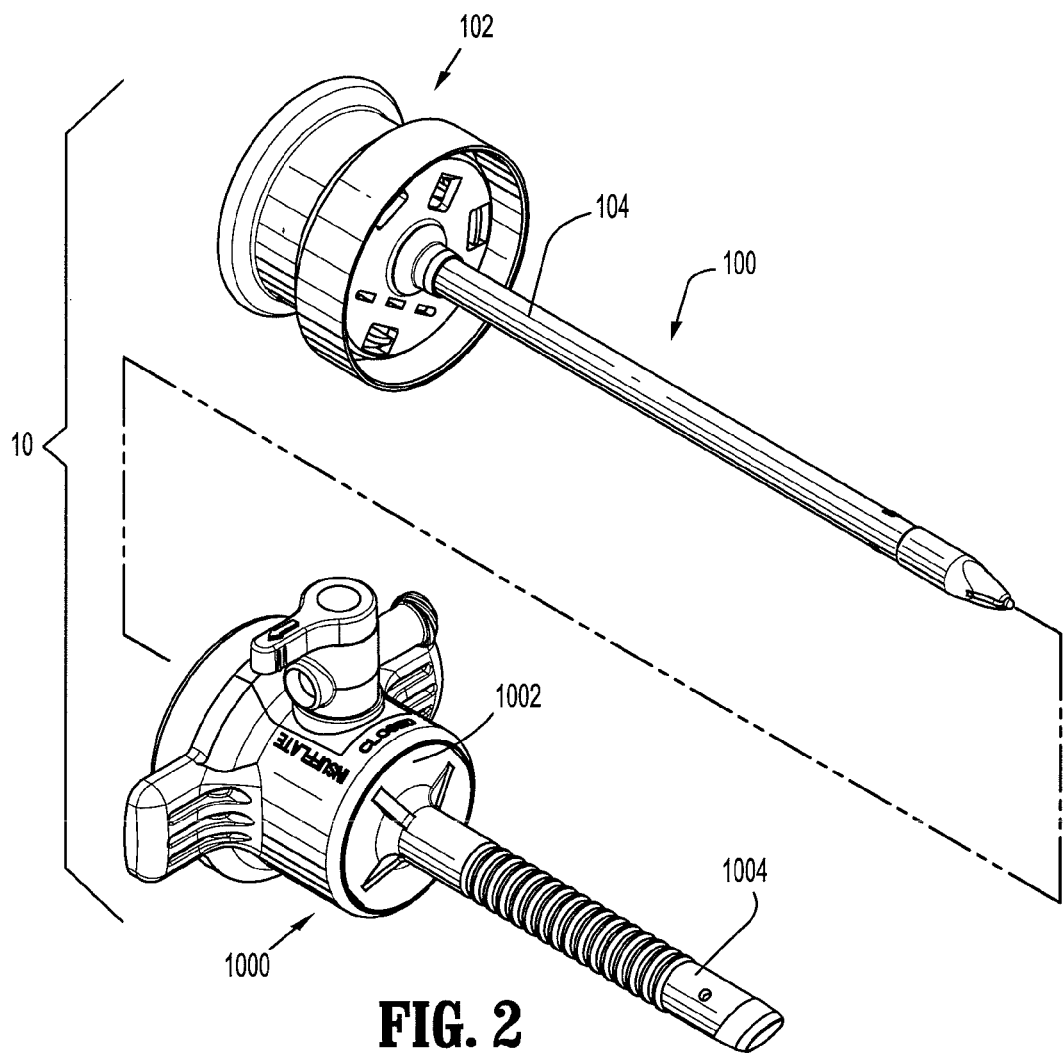
FIG. 2 is a perspective view with parts separated of the trocar assembly illustrating the cannula assembly and the obturator assembly.
Figure 3:
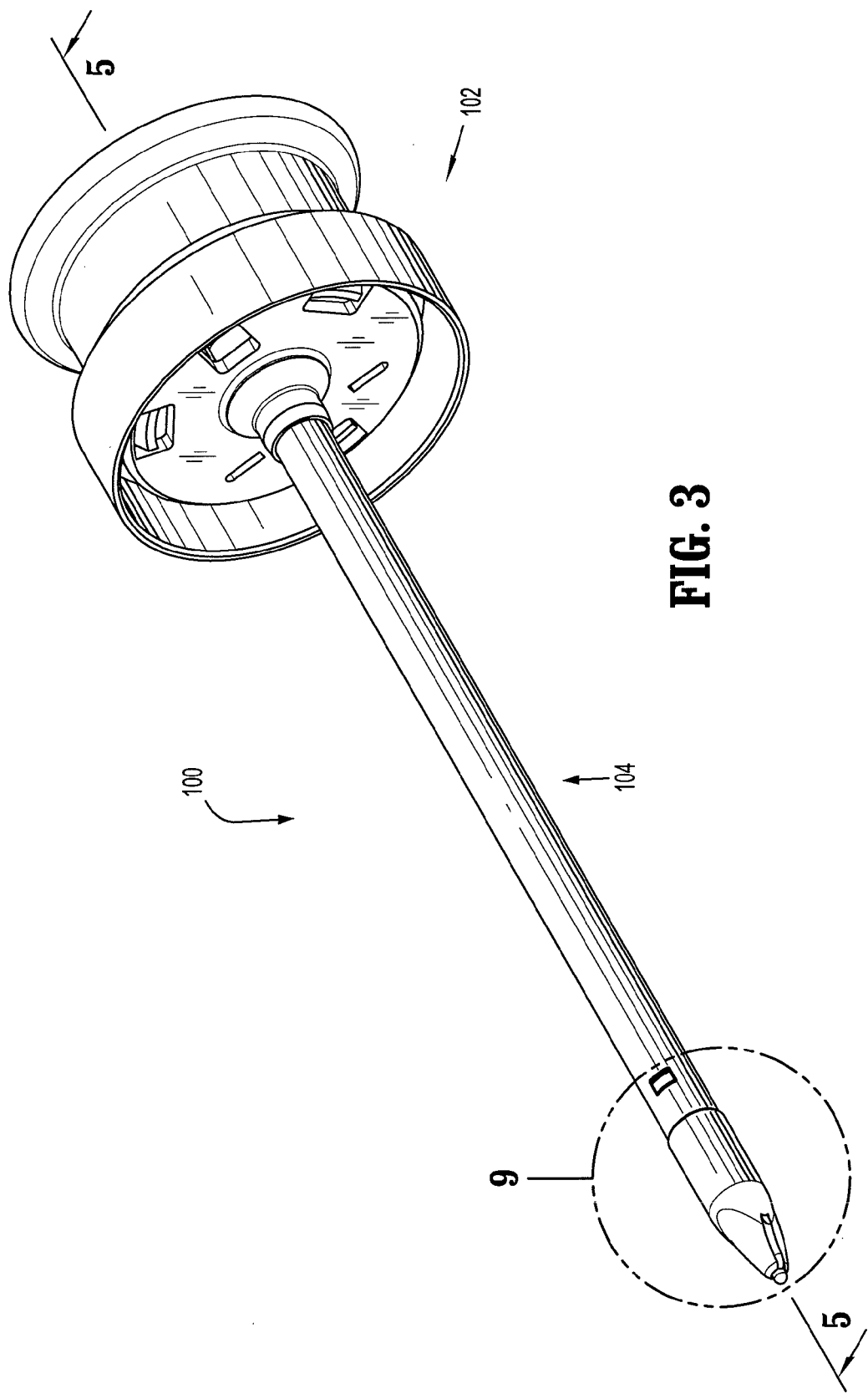
FIG. 3 is a perspective view of the obturator assembly of the trocar assembly.
Figure 4:
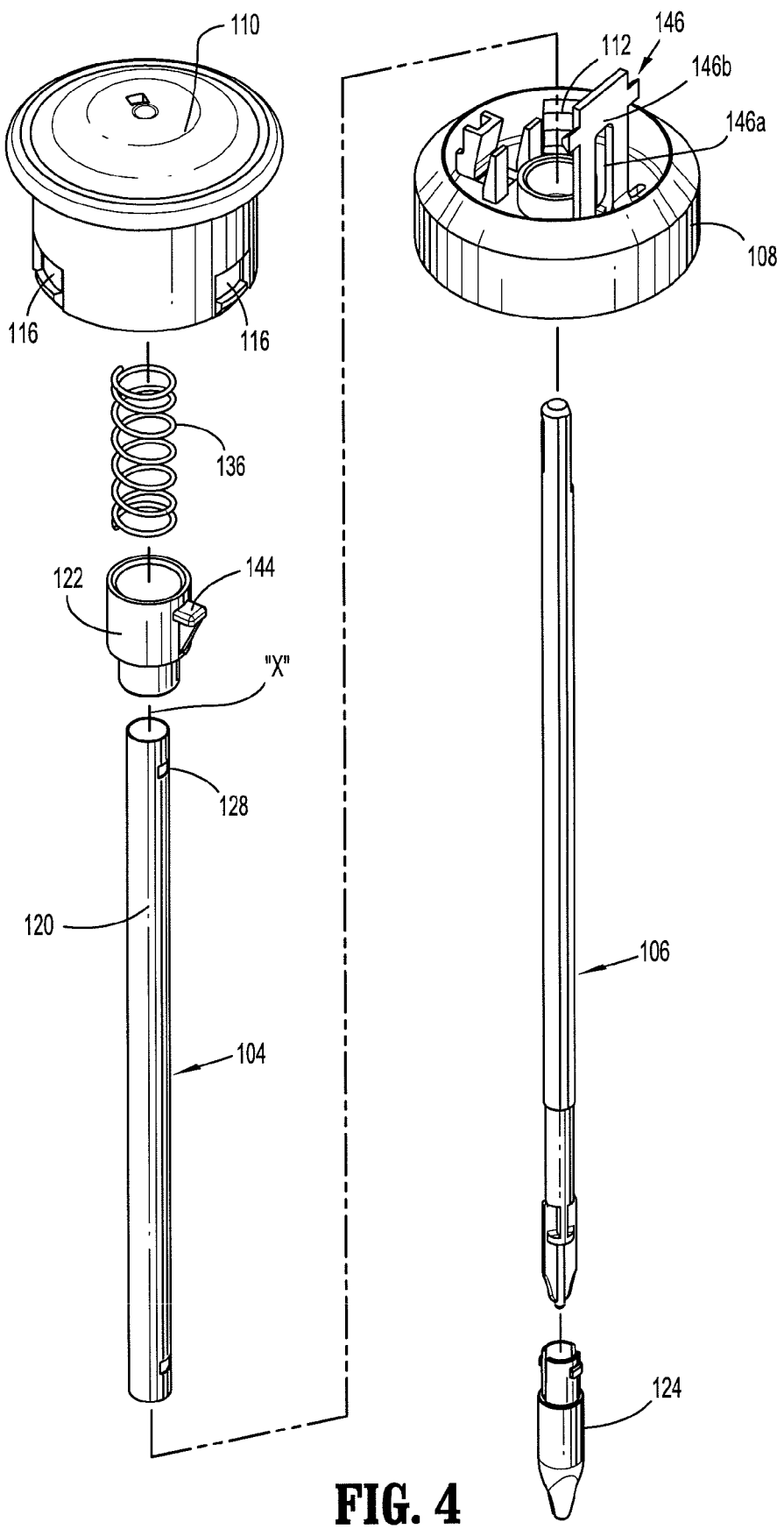
FIG. 4 is a perspective view with parts separated of the obturator assembly illustrating the obturator shield and the obturator member.

Referring now in detail to the drawing figures, in which, like references numerals identify similar or identical elements, there is illustrated, in FIGS. 1 and 2, a trocar assembly constructed in accordance with a preferred embodiment of the present disclosure, and designated generally by reference numeral 10. Trocar assembly 10 is particularly adapted for use in minimally invasive surgical procedures such as endoscopic or laparoscopic procedures. Generally, trocar assembly 10 includes two principal subassemblies, namely, obturator assembly 100 and cannula assembly 1000.

Cannula assembly 1000 may be any cannula assembly suitable for use in a laparoscopic surgical procedure. In one embodiment, cannula assembly 1000 includes cannula housing 1002 and cannula sleeve 1004 extending from the cannula housing 1002. Either or both cannula housing 1002 and cannula sleeve 1004 may be transparent in part or in whole and may be fabricated from biocompatible metal or polymeric material. Cannula assembly 1000 may include an internal seal such as a duck-bill valve or other zero closure valve adapted to close in the absence of a surgical instrument to prevent passage of insufflation gases through the cannula assembly 1000.

With reference now to FIGS. 3-6, in conjunction with FIG. 2, obturator assembly 100 includes obturator housing 102, obturator sleeve 104 extending distally from the housing 102 and obturator member 106 at least partially disposed within the obturator sleeve 104. Obturator sleeve 104 defines obturator axis "x" and will be discussed in greater detail hereinbelow. Obturator housing 102 includes housing base 108 and housing cap 110. Once the appropriate components are positioned therewithin, housing base 108 may be connected to housing cap 110 through engaging mating surfaces. For example, housing base 108 may include resilient latches 112 extending from inner annular wall 114 of housing base 108 (FIG. 6). Latches 112 interlock with correspondingly dimensioned latch openings 116 within housing cap 110. To uniformly connect housing base 108 and housing cap 110 at least three corresponding latches 112 and openings 116 are spaced evenly around inner wall 114 of housing base 108 and the periphery of housing cap 110. Housing base 108 further defines outer wall 118 depending distally relative to inner wall 114. Outer wall 118 receives cannula housing 1002 as will be discussed.

Referring now to FIGS. 4-8, obturator sleeve 104 includes shield member 120, shield collar 122 and shield nose 124. Each of these components is operatively connected to each other to define an outer member of obturator assembly 100. In one preferred embodiment, shield member 120 is at least partially positioned within shield collar 122. Shield collar 122 has a plurality of radially inwardly directed tabs 126 which are received within corresponding openings 128 of shield member 120 in a snap-fit relation (FIG. 7). Similarly, shield nose 124 may be at least partially positioned within shield member 120. Shield nose 124 incorporates a plurality (e.g., two) of resilient locking tabs 130 depending radially outwardly adjacent a proximal end of the obturator nose 124. Locking tabs 130 are received within corresponding openings 132 adjacent the distal end of shield member 120 also in snap relation to connect the components (FIG. 8) thus providing for selective disengagement of the shield nose 124 from the shield member 120, e.g., for the purposes of changing the obturator rod 158 (explained further below). Other means for connecting the components of obturator sleeve 104 are also envisioned including bayonet couplings, adhesives, welding, tongue and groove arrangements, etc. In other embodiments, obturator sleeve 104 is a single component. In the assembled condition, shield collar 122 of obturator sleeve 104 is disposed within housing base 108, and at least partially received within annular wall 134 of the housing base 108. Obturator sleeve 104 is adapted for axial movement along axis "x" and relative to obturator housing 102.

Obturator sleeve 104 is spring biased in the distal direction by coil spring 136. In particular, coil spring 136 is received within internal bore 138 of shield collar 122 and engages internal shelf 140 of the shield collar 122. The proximal end of coil spring 136 is coaxially mounted about spring mount 142 (see FIG. 6) depending from the interior surface of housing cap 110.

Shield collar 122 includes transverse shelf 144 extending outwardly relative to the obturator axis "x". Shelf 144 limits the length or distance of retracting motion of obturator sleeve 104 through its engagement with collar stop 146 within housing cap 110. Specifically, shelf 144 travels within opening 146a of collar stop 146 during retracting longitudinal movement of obturator sleeve 104 and is limited by its engagement with cross-beam 146b of the collar stop 146 (see also FIG. 4).

Figure 9:
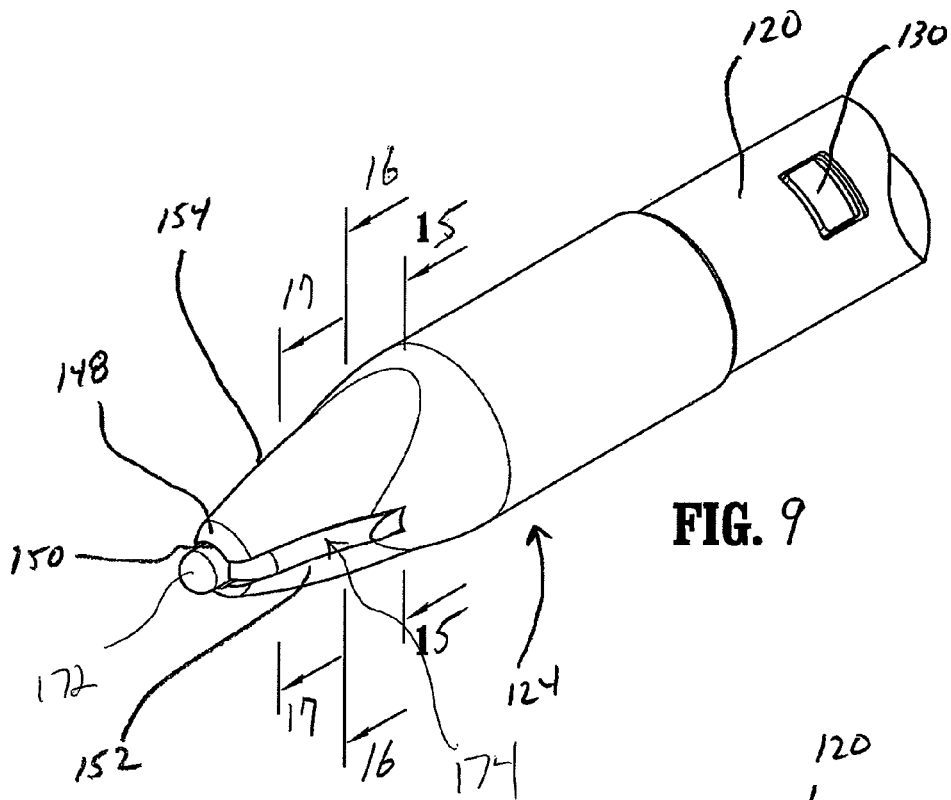
FIG. 9 is a perspective view of the leading end of the obturator assembly.
Figure 10:
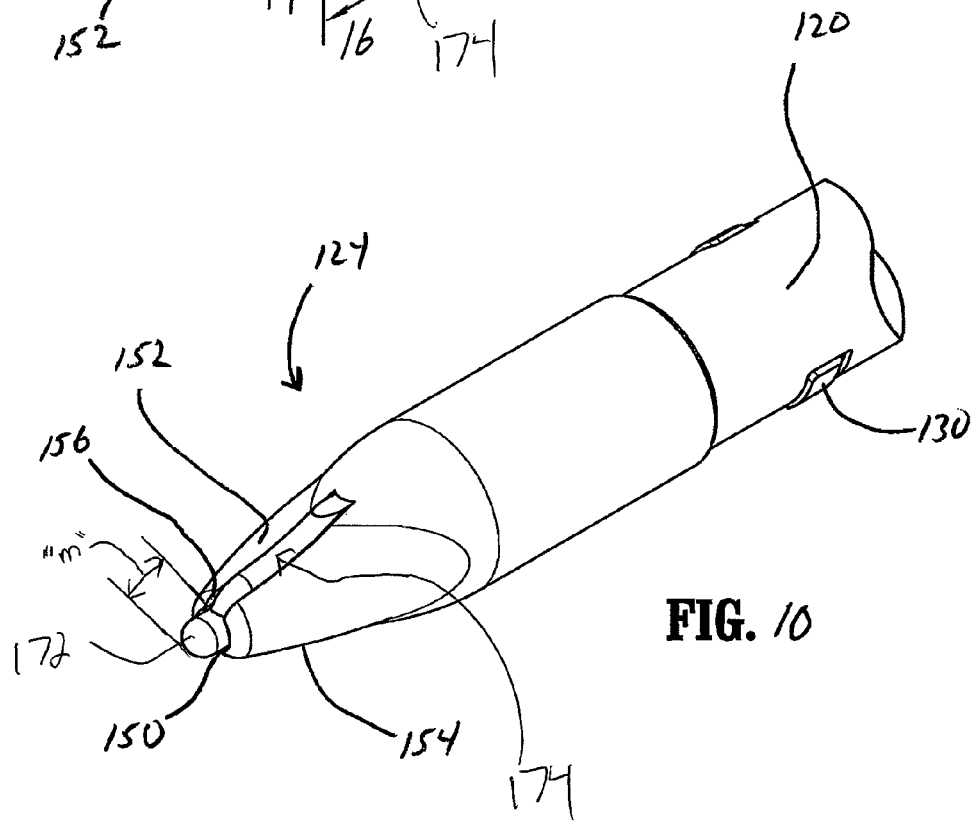
FIG. 10 is a second perspective view of the leading end of the obturator assembly.

With reference to FIGS. 9 and 10, shield nose 124 may be tapered, conical or frusto-conical in configuration, and is adapted to pass through tissue and may be capable of dissecting through tissue. In one preferred embodiment, shield nose 124 has an irregular shaped with rounded tip 148 and central aperture 150 extending through the rounded tip 148. In particular, shield nose 124 is generally tapered in configuration defining a complex curved arrangement. In a first profile of shield nose 124, the shield nose 124 includes opposed concave surfaces 152. In a second profile (viewed at a 90° offset), shield nose 124 defines convex or outwardly bowed surfaces 154. This alternating concave and convex arrangement provides a substantially reduced profile (in cross-section) compared to conventional conically shaped obturators thereby providing an enhanced ability to penetrate or pass through tissue layers. Various radii of curvature are contemplated. Rounded tip 148, by its arcuate configuration, minimizes the potential of undesired or unintended piercing of tissue. Shield nose 124 also defines slot 156 traversing the shield nose 124. This particular configuration of shield nose 124 is disclosed in commonly assigned U.S. patent application Ser. No. 11/103,892, filed Apr. 12, 2005, the contents of which are incorporated in its entirety by reference herein.

With reference to FIGS. 11-14, in conjunction with FIG. 5, obturator member 106 will be discussed. Obturator member 106 includes obturator rod 158 and obturator penetrating head 160 at the distal end of the obturator rod 158. Obturator rod 158 defines proximal end 162 having a general semi-circular cross-section and being received within correspondingly dimensioned opening 164 of spring mount 142 of housing cover 110. The proximal end 162 further defines latch 166 which is received within side opening 168 of spring mount 142 in snap relation therewith to secure the two components (see FIG. 5). In this regard, obturator member 106 is longitudinally fixed within obturator housing 102. The sloped surface of latch 166 also provides for selective disengagement of obturator rod 158 from housing cover 110, e.g., by a tool inserted within an opening of the housing cover 110, enabling obturator rod 158 to be interchangeable, e.g., with rods having different shaped tips.

Obturator penetrating head 160 includes central rod segment 170 extending to arcuate leading surface 172 and substantially planar dissecting segment 174 longitudinally spaced from the arcuate leading surface 172. Arcuate leading surface 172 is atraumatic to tissue and is spaced from dissecting segment 174 a predetermined distance "m". This consequent narrow profile provided by central rod segment 170 permits initial insertion within tissue and facilitates, e.g., dissection or advancement within the tissue without an incising action. Planar dissecting segment 174 includes opposed outer surfaces 176 having an arcuate character in cross-section, which extend or taper from central rod segment 170 to an outer boundary of the planar segment 174. Outer surfaces 176 define a substantially asymmetrical or non-linear tapered arrangement, e.g., the contour of the opposed outer surface may define a non linear, complex shape. In one embodiment, outer surfaces 176 define a generally convex segment 178 adjacent central rod segment 170 leading to a generally recessed or concave segment 180 outwardly of the central rod segment 170. This arrangement provides a hollow ground appearance to outer surfaces 176 thereby assisting in advancement of penetrating head 160 within tissue. Planar segment 174 functions as a dissecting element to dissect tissue as arcuate leading surface 172 is advanced into tissue.

Penetrating head 160 further defines disc segment 182 which is spaced from arcuate leading end 172. Disc segment 182 is generally transverse to the longitudinal axis and maintains proper spacing of penetrating head 160 within shield nose 124 to prevent lateral displacement of the penetrating head 166. Disc segment 182 has longitudinal rails 184 extending to the obturator rod 158. Rails 184 define a cross-sectional dimension approximating the diameter of disc segment to also assist in positioning penetrating head 160 within shield nose 124.

Referring to FIGS. 9, 10 and 15-17, penetrating head 160 is mounted within shield nose 124 with central rod segment 170 being received within and extending through central aperture 150 of the shield nose and planar dissecting segment 174 received within slot 156 traversing the shield nose. In the extended position of obturator shield and shield nose 124 depicted in FIGS. 9 and 10, at least arcuate leading surface 172 and outer surface 176 of penetrating head 160 are exposed from the shield nose.

Figure 18:
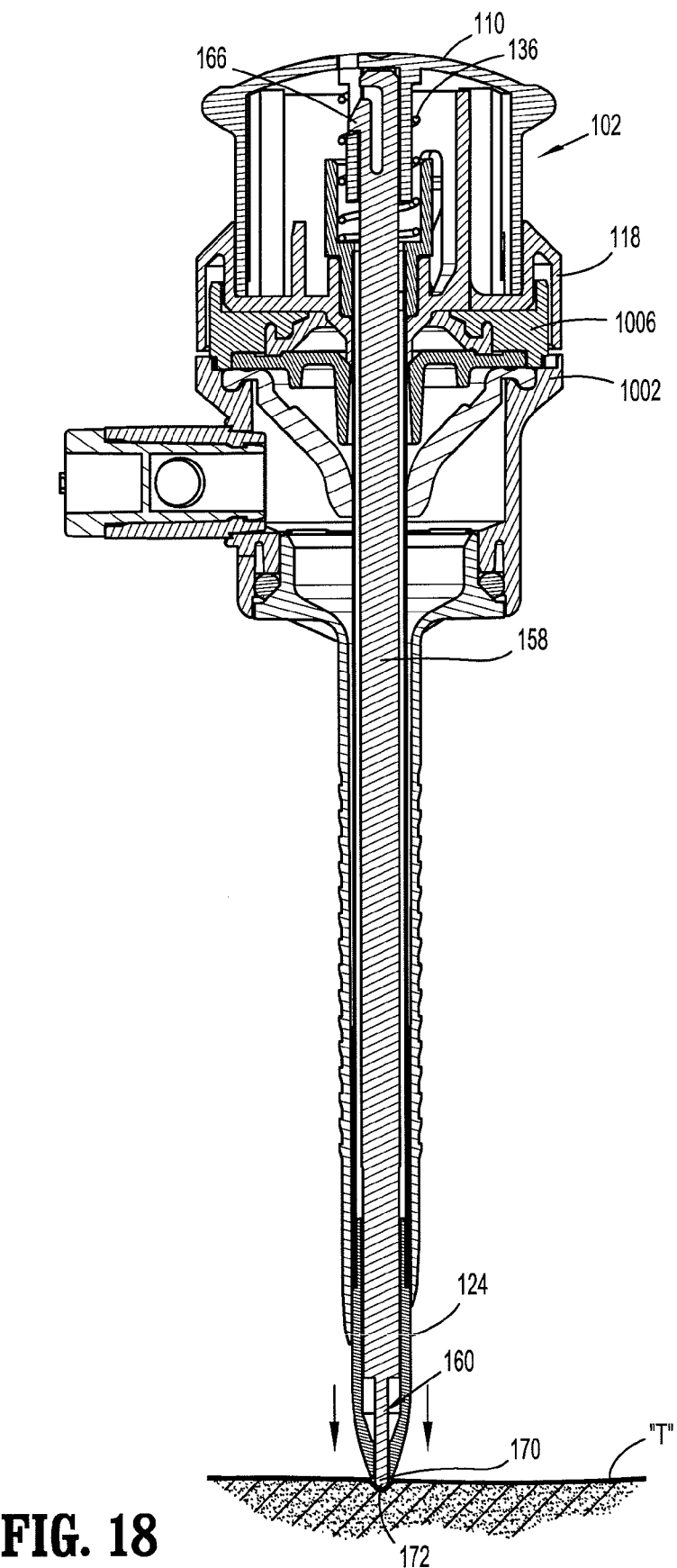
FIG. 18 is a cross-sectional view illustrating insertion of the trocar assembly within tissue.

With reference now to FIG. 18, a method of use and operation of trocar assembly 10 will be discussed. Obturator assembly 100 is inserted within cannula assembly 1000 and advanced to where obturator housing 102 is approximated with cannula housing 1002. Outer wall 118 of obturator housing 102 may be appropriately dimensioned to form a friction fit with annular element 1006 of cannula housing 1002 or may be coupled to each other by conventional means including bayonet coupling, tongue-groove, etc. Obturator penetrating head 160 is applied against the tissue "T" such that arcuate leading surface 172 of central rod segment 170 engages tissue. Arcuate leading surface 172 may be manipulated to advance within a previously formed incision.

Figure 19:
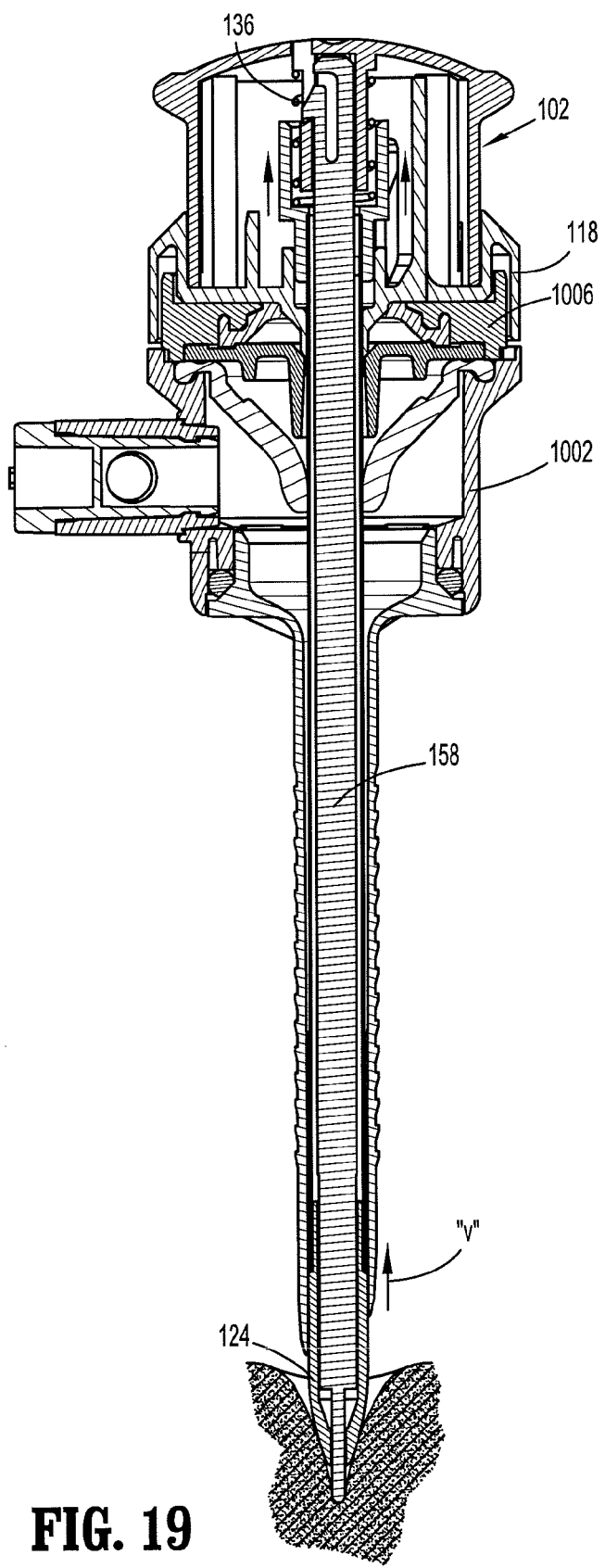
FIG. 19 is a view similar to the view of FIG. 18 illustrating the obturator sleeve in a retracted position fully exposing the penetrating head of the obturator member.
Figure 20:
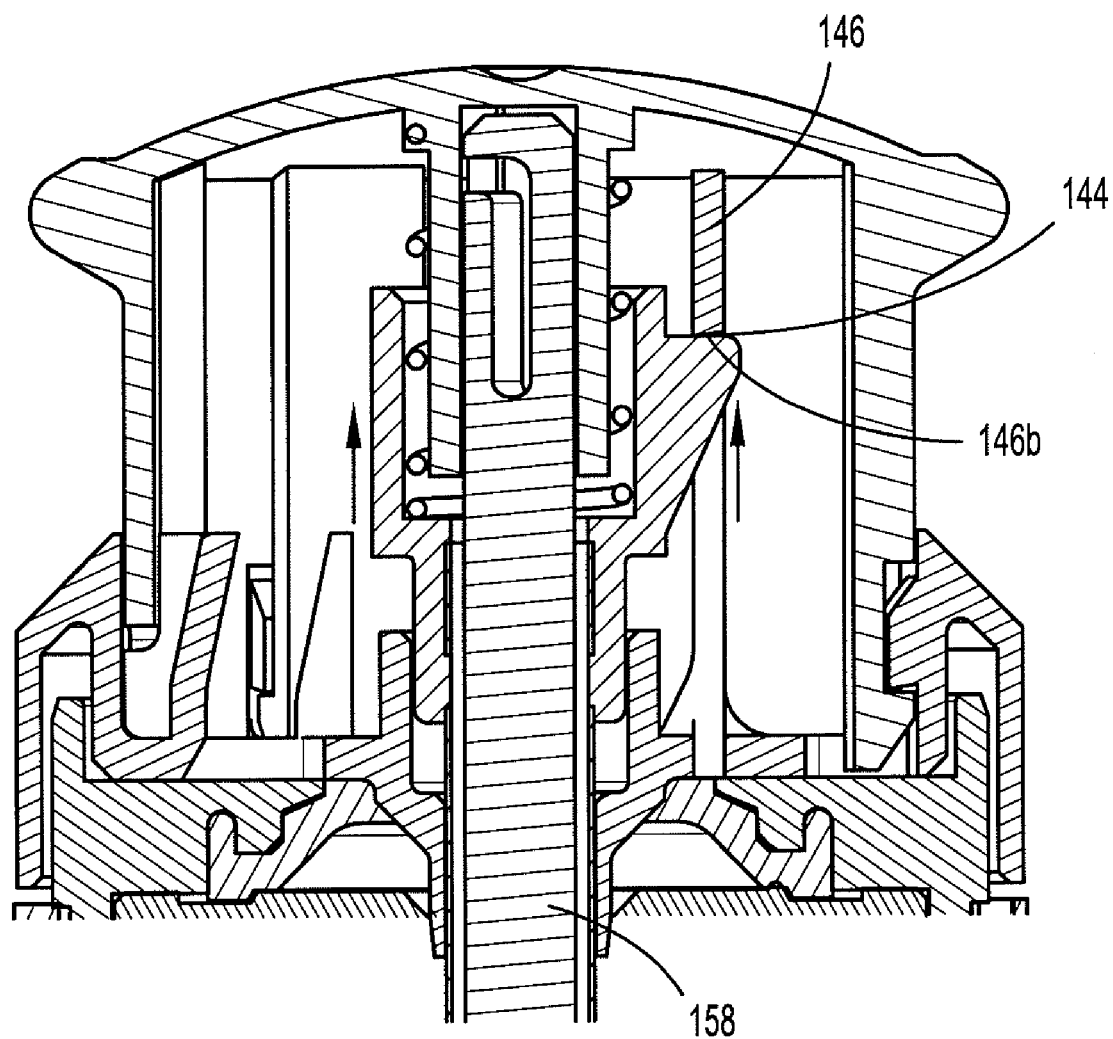
FIG. 20 is a side cross-sectional view of the obturator housing and cannula housing illustrating the transverse shelf of the obturator sleeve engaging the stop within the obturator housing.

The surgeon thereafter begins to advance trocar assembly 10 through the body wall of the patient. Shield nose 124 of obturator sleeve 104 contacts the tissue "T" and is driven upwardly to cause the obturator sleeve 104 to move proximally (depicted by directional arrow "v") against the bias of coil spring 136 as shown in FIG. 19. Obturator sleeve 104 continues its proximal retracting movement until shelf 144 of shield collar 122 engages cross-beam 146b of collar stop 146 as shown in FIG. 20. In this retracted position of obturator sleeve 104, obturator penetrating head 160 is exposed to dissect through the tissue. The surgeon may apply a distally-directed force to obturator assembly 100 to cause penetration through the tissue in an atraumatic manner as previously discussed.

Once penetrating head 160 and shield nose 124 pass through the body wall of the patient, obturator sleeve 104 is driven distally under the influence of coil spring 136 to return to its original position of FIG. 18. The obturator assembly 100 is removed from cannula assembly 1000 and surgery is performed with instruments inserted through cannula assembly 1000.

Except where noted otherwise, the materials utilized in the components of the presently disclosed trocar assembly generally include materials such as, for example, ABS, polycarbonate, stainless steel, titanium and any other suitable biocompatible metals and/or polymeric materials. A preferred ABS material is CYCOLAC which is available from General Electric. A preferred polycarbonate material is also available from General Electric under the trademark LEXAN. An alternative polycarbonate material which may be utilized is CALIBRE polycarbonate available from Dow Chemical Company. The polycarbonate materials may be partially glass filled for added strength.

Although the illustrative embodiments of the present disclosure have been described herein with reference to the accompanying drawings, it is to be understood that the disclosure is not limited to those precise embodiments, and that various other changes and modifications may be effected therein by one skilled in the art without departing from the scope or spirit of the disclosure.

What is claimed is:

1. An obturator assembly, which comprises:
   an obturator housing;
   an obturator member mounted to the obturator housing, the obturator member defining a longitudinal axis and having proximal and distal ends, the obturator member including an interchangeable obturator rod and a penetrating end, the penetrating end defining a substantially planar dissecting segment and a central rod segment extending distally beyond a distal-most end of the substantially planar dissecting element, the planar segment having blunt outer edges, the central rod having a blunt distal entry surface;
   an obturator sleeve coaxially mounted about the obturator member and adapted for reciprocal longitudinal movement between a retracted position and an extended position;
   wherein the distal entry surface of the penetrating end is exposed from the obturator sleeve when in the extended position of the obturator sleeve.

2. The obturator assembly according to claim 1 wherein the blunt outer edges of the planar segment are arcuate.

3. The obturator assembly according to claim 1 wherein the distal entry surface of the penetrating end is arcuate.

4. The obturator assembly according to claim 1 wherein the obturator sleeve includes a generally tapered nose shield for at least partially accommodating the penetrating end.

5. The obturator assembly according to claim 4 wherein the blunt edges of the planar segment of the penetrating end extends radially outwardly from the nose shield when in the extended position of the obturator sleeve.

6. The obturator assembly accordingly to claim 1 wherein the obturator member is monolithically formed.

7. The obturator assembly accordingly to claim 1 wherein the obturator sleeve is normally biased toward the extended position thereof.

8. The obturator assembly according to claim 1, wherein the substantially planar dissecting segment defines a plane that is substantially parallel to the longitudinal axis.

9. The obturator assembly according to claim 1, wherein an outer surface of the substantially planar dissecting segment includes a non-linear shape.

10. The obturator assembly according to claim 1, wherein an outer surface of the substantially planar dissecting segment includes a convex segment and a concave segment.

11. The obturator assembly according to claim 1, wherein the substantially planar dissecting segment includes an arcuate leading surface.

12. The obturator assembly according to claim 1, wherein the central rod segment extends proximally of the distal-most end of the planar dissecting element.

13. The obturator assembly according to claim 1, wherein side walls of the central rod segment are parallel to the longitudinal axis along a majority of their length.

14. An obturator assembly, which comprises:
   an obturator housing
   an obturator member mounted to the obturator housing, the obturator member defining a longitudinal axis and having proximal and distal ends, the obturator member including an obturator rod and a penetrating end, the penetrating end defining a substantially planar dissecting segment and a central rod segment extending distally beyond a distal-most end of the substantially planar dissecting element, the planar dissecting segment including an outer surface having a convex segment and a concave segment, the convex segment being located distally of the concave segment;
an obturator sleeve coaxially mounted about the obturator member and adapted for reciprocal longitudinal movement between a retracted position and an extended position.

15. An obturator assembly, which comprises:
an obturator housing;
an obturator member mounted to the obturator housing, the obturator member defining a longitudinal axis and having proximal and distal ends, the obturator member including an obturator rod and a distally positioned penetrating end including a distal end surface;
the penetrating end defining a substantially planar segment with substantially blunt outer edges leading toward and proximal of the distal end surface; and
an obturator sleeve coaxially mounted about the obturator member and adapted for reciprocal longitudinal movement between a retracted position and an extended position, the obturator sleeve having a nose adjacent the penetrating end, the nose being correspondingly dimensioned and configured such that the outer edges of the penetrating end are at least partially exposed from the nose when the obturator sleeve is in the extended position.

16. The obturator assembly according to claim 15 wherein the penetrating end defines a distal end surface which is exposed from the nose when the obturator sleeve is in the extended position.

17. The obturator assembly according to claim 16 wherein the distal end surface is substantially blunt.

18. The obturator assembly according to claim 15 wherein the penetrating end includes a substantially cylindrical element extending distal of the planar segment, the cylindrical element having the distal end surface.

* * * * *